(12) United States Patent
Ollivier

(10) Patent No.: US 10,695,559 B2
(45) Date of Patent: *Jun. 30, 2020

(54) INTRACARDIAC CAPSULE AND AN IMPLANTATION ACCESSORY FOR USE WITH THE FEMORAL ARTERY

(71) Applicant: SORIN CRM S.A.S., Clamart (FR)

(72) Inventor: Jean-François Ollivier, Villiers le Bâcle (FR)

(73) Assignee: Sorin CRM SAS, Clamart (FR)

( * ) Notice: Subject to any disclaimer, the term of this patent is extended or adjusted under 35 U.S.C. 154(b) by 315 days.

This patent is subject to a terminal disclaimer.

(21) Appl. No.: 15/894,541

(22) Filed: Feb. 12, 2018

(65) Prior Publication Data

US 2018/0161571 A1    Jun. 14, 2018

Related U.S. Application Data

(63) Continuation of application No. 14/312,381, filed on Jun. 23, 2014, now Pat. No. 9,889,295.

(30) Foreign Application Priority Data

Jun. 24, 2013 (FR) .................................... 13 56020

(51) Int. Cl.
*A61N 1/05* (2006.01)
*A61N 1/375* (2006.01)
*A61N 1/372* (2006.01)

(52) U.S. Cl.
CPC ........... *A61N 1/0573* (2013.01); *A61N 1/056* (2013.01); *A61N 1/0565* (2013.01);
(Continued)

(58) Field of Classification Search
CPC .... A61N 1/057; A61N 1/0573; A61N 1/0575; A61N 1/37205; A61N 1/3756;
(Continued)

(56) References Cited

U.S. PATENT DOCUMENTS 6,463,333 B1  10/2002  Ollivier
8,548,605 B2  10/2013  Ollivier
(Continued)

FOREIGN PATENT DOCUMENTS

EP    2 394 695 A1    12/2011
EP    2 394 695 B1     9/2012

OTHER PUBLICATIONS

Preliminary Search Report for French Patent Application No. 1356020, dated Oct. 22, 2013, 2 pages.
(Continued)

*Primary Examiner* — Wade Miles
(74) *Attorney, Agent, or Firm* — Foley & Lardner LLP

(57) ABSTRACT

An assembly including an autonomous capsule having an anchoring member adapted to penetrate tissue of the heart and an accessory for implantation of the capsule. The accessory includes a steerable catheter with an inner lumen, having at its distal end a tubular protection tip defining a volume for housing the capsule. The accessory also includes a disconnectable attachment mechanism for supporting and guiding the capsule to an implantation site and a sub-catheter housed within the lumen of the steerable catheter, moveable in translation and in rotation relative to the steerable catheter. The sub-catheter and the capsule are movable between a retracted position and a position wherein the capsule is deployed out of the protection tip. The sub-catheter and the capsule are provided with a first fastening mechanism for fastening the two in translation and in mutual rotation, which is disconnectable under a rotation applied to the sub-catheter.

20 Claims, 7 Drawing Sheets

(52) U.S. Cl.
CPC ....... *A61N 1/3756* (2013.01); *A61N 1/37205* (2013.01); *A61N 1/37518* (2017.08); *A61N 2001/058* (2013.01)

(58) Field of Classification Search
CPC ........ A61N 2001/058; A61B 17/12113; A61B 2017/12054; A61B 2017/1205; A61F 2002/011
See application file for complete search history.

(56) References Cited

U.S. PATENT DOCUMENTS

| | | | |
|---|---|---|---|
| 8,615,310 B2 | 12/2013 | Khairkhahan et al. | |
| 9,974,948 B2* | 5/2018 | Ollivier | A61N 1/0573 |
| 2001/0044633 A1* | 11/2001 | Klint | A61B 17/12022 |
| | | | 606/200 |
| 2002/0065543 A1 | 5/2002 | Gomperz et al. | |
| 2004/0082879 A1* | 4/2004 | Klint | A61B 17/12022 |
| | | | 600/585 |
| 2005/0085883 A1 | 4/2005 | Ollivier et al. | |
| 2007/0135882 A1 | 6/2007 | Drasler et al. | |
| 2007/0135883 A1 | 6/2007 | Drasler et al. | |
| 2009/0204170 A1 | 8/2009 | Hastings et al. | |
| 2010/0274338 A1 | 10/2010 | Ollivier | |
| 2011/0301686 A1* | 12/2011 | Bowman | A61B 17/1214 |
| | | | 623/1.11 |
| 2011/0307043 A1 | 12/2011 | Ollivier | |
| 2012/0095539 A1 | 4/2012 | Khairkhahan et al. | |
| 2012/0184987 A1* | 7/2012 | Sirota | A61F 2/01 |
| | | | 606/200 |
| 2014/0378991 A1 | 12/2014 | Ollivier | |
| 2014/0378992 A1 | 12/2014 | Ollivier | |

OTHER PUBLICATIONS

Preliminary Search Report for French Patent Application No. 1356021, dated Oct. 23, 2013, 2 pages.

* cited by examiner

INTRACARDIAC CAPSULE AND AN IMPLANTATION ACCESSORY FOR USE WITH THE FEMORAL ARTERY

CROSS-REFERENCE TO RELATED APPLICATION

This application is a continuation application of U.S. patent application Ser. No. 14/312,381 filed Jun. 23, 2014, which claims the benefit of and priority to French Patent Application No. 1356020, filed Jun. 24, 2013, both of which are hereby incorporated by reference herein in their entireties.

BACKGROUND

The invention relates to "active implantable medical devices" as defined by Directive 90/385/EEC of 20 Jun. 1990 of the Council of the European Communities, specifically implants to continuously monitor heart rhythm and deliver, if necessary, electrical pulses to the heart for stimulation, resynchronization and/or defibrillation in case of rhythm disorder detected by the device.

The invention relates, in general, to the in situ implantation of such devices provided at the distal end with an anchoring device adapted to penetrate the tissue of a body wall at the chosen implantation site.

A typical example of such an anchoring member is a projecting helical screw axially extending from the medical device body and adapted to penetrate the heart tissue by a screwing motion at the implantation site. However, this anchoring arrangement is not limitative of the invention, which also applies to other types of anchoring members, for example by implementation of needles, hooks, barbs, etc., penetrating tissue for permanently fixing the medical device.

According to a first aspect, the invention more particularly relates to those devices that are in the form of an autonomous capsule implanted in a heart chamber (ventricle, atrium or even arterial left heart chamber). The device will be hereinafter referred to as "autonomous capsule" or "leadless capsule" (the autonomous character of the capsule, albeit not intrinsically, being a necessary feature of the invention). These autonomous capsules are devoid of any physical connection to a main implanted device (such as the housing of a stimulation pulse generator) or not implanted device (external device such as a programmer or monitoring device for remote monitoring of the patient). Accordingly, the capsules are referred to as "leadless capsules", to distinguish them from electrodes or sensors located at the distal end of a conventional lead, which is traversed throughout its length with one or more conductors galvanically connecting the electrode or sensor to a connected generator at an opposite, proximal, end to the lead.

It will be seen that, according to a second aspect, the invention can be generalized to the "delivery". That is to say the implantation in the selected site of implantation of other types of medical devices. In one example, such devices may be stimulation leads in the form of a tubular body having at its distal end an anchoring mechanism for anchoring to a heart wall and an active portion provided with detection/stimulation electrodes, and at its proximal end, mechanical and electrical connection to the housing of a generator that is remotely implanted from the site of application of the pulses. The invention can be applied to still other types of implantable devices, for example to capsules intended for release in situ of an active pharmacological agent.

When the leadless capsules are endocardial capsules (capsules attached to the inner wall of an atrial or ventricular chamber, as opposed to epicardial capsules fixed to the external wall of the heart), the implantation constraints are increased because of the surgery approach. The approach for endocardial implantation involves going through the peripheral venous system and directs, under image intensifier, the capsule to the selected implantation site. This in a both precise and perfectly secure method. It is only once the site is reached and the capsule is firmly attached in the heart wall that the operator may proceed to the "release" of the capsule, or more particularly, its disconnection from the implantation accessory.

U.S. 2012/0095539 A1 discloses an implantation accessory for an endocardial electrostimulation leadless capsule. This accessory includes a steerable catheter carrying the capsule. The steerable catheter houses in its inner lumen at its end a wire which is distally connected to the capsule and which is operable in translation and rotation from the proximal end by a handle provided for the practitioner. In a first embodiment, the capsule is mounted to the catheter tip by a system of male/female nesting and the wire end is screwed to the back of the capsule. The retention wire keeps the two elements of the coupling system fitted into each other by a slight tension on the wire, the latter being locked in translation in the manipulation handle. In a second embodiment, the wire remains attached to the capsule after it has been separated from the catheter, so as to act as a safety wire in case it is necessary to reoperate on the capsule after implantation.

EP 2394695 A1 (Sorin CRM SAS) discloses another autonomous intracardiac capsule assembly with an implantation accessory. The capsule holds on the sidewall of the tubular body coupling fingers cooperating with a helical guide carried by the distal end of the implantation accessory. The direction of helix of the helical guide is opposite to that of the anchoring screw of the capsule, so as to transmit the screwing torque of the anchoring screw in the heart wall. Then after the front face of the capsule is coming to bear against this wall, the progressive separation of the capsule with the implantation accessory occurs by further screwing of the catheter causing the coupling fingers to slide between the turns of a helical compression spring. The torque limiter effect is thus being obtained by the compression of this helical spring.

The acceptance by practitioners of the technique of endocardial leadless capsules involves being able to offer a delivery system that is able to secure the implementation of these capsules and may include the following advantageous features:

Procedure similar to the current practice, which makes use of well-known and mastered practitioners gestures: subclavian or femoral puncture, insertion and manipulation of a catheter via preformed stylets during the approach phase of the selected implantation site, fastening of the screw or barb type, catheter manipulation of the electrophysiology type, etc.;

Standard environment of the operating room;

Limiting the risk of coring of the tissues due to excessive tightening which may damage the wall or worse, puncture it (especially in the case of implantation into a thin wall as the atrial septum or the apical region the right ventricle);

Possibility of intraoperatively or postoperatively removing and/or repositioning in case of problems, even after release of the capsule;

No risk of migration of the capsule during the acute phase response;

Certainty of a good fixation of the capsule before removing the implantation accessories, this constraint being the most critical of all;

System natively designed for a femoral approach (see below);

For vessels and heart chambers, no risk of damage by the anchoring member (screw, hook, needle, etc.) throughout the implantation method, including the navigation in the venous network and the approach phase to the selected implantation site;

Quick procedure, with an implantation target time of approximately 30 minutes 'skin-to-skin', comparable to that of the implantation of a generator and a conventional ventricular lead;

Safe operation, including in the case of: i) improper handling, with in this case inability to jettison the capsule if screwing of the anchoring member is incomplete, and/or ability to recover the capsule during the procedure, and ii) premature discontinuation of the procedure;

Low cost of manufacturing of the complete implantation system, notably through the use of proven technologies and components in similar applications.

A further difficulty arises with the current leadless capsules due to their relatively large dimensions, with a typical diameter of about 4-7 mm and a length of 15-40 mm. Indeed, to reach a heart chamber, and in particular to reach the apex of the right ventricle, with an object of this size there is no routine procedure by high approach, that is to say via the subclavian vein. It is therefore necessary to use a different approach, from a femoral puncture then to go back in the inferior vena cava to the heart.

Such a femoral approach is recognized as more difficult, especially because of the large angle between the inferior vena cava and the axis of the right ventricle. Indeed, in the case of a high approach, at the arrival in the atrium, the distal portion of the implantation catheter is naturally oriented towards the apex of the right ventricle. At this point, one just has to push the catheter through the tricuspid valve and reach the bottom of the ventricle, wherein the anchoring member may be screwed to the wall after landing. However, in the case of a femoral approach, once the atrium is reached it is necessary to perform a turning maneuver of the distal end of the catheter to guide the latter towards the ventricle and allow it to pass through the tricuspid valve and continue to progress in the right direction, towards the apex of the ventricle.

For this purpose, well-known steerable catheters exist, the tip of which is operated from the proximal handle so that it can perform such a reorientation maneuver in the atrium under image intensifier. But a final challenge remains in the final approach phase, as part of the steerable catheter may be too short or poorly shaped to allow docking with the wall of the ventricular apex.

There is therefore the need to have an implantation accessory for fine adjustment and precise approach of the implantation site with large differences in myocardium anatomy.

SUMMARY

The invention discloses, in a first aspect, to use a steerable catheter and to extend it distally by a projecting cylindrical tip containing the capsule to be implanted. This capsule is maintained in the retracted position in the tip via a sub-catheter inserted into the inner lumen of the first catheter, the capsule and the sub-catheter being temporarily linked by a single disconnectable mechanism fixed on the sub-catheter and allowing a complete screwing of the capsule in the tissue before release. The telescopic configuration of the sub-catheter allows projecting the capsule out of the protection tip and beyond the latter on several centimeters, permitting in all cases a complete and accurate approach of the capsule to the bottom of the ventricle.

According to a second, more general, aspect the invention discloses a simple switchable mechanism provided between a implantation accessory and a medical device (corresponding, respectively, to the sub-catheter and to the leadless capsule in the previous particular case). This mechanism consists of an elastic deformable component used in radial compression, that is to say for its pinch effect and not for its axial tensile/compression effect. Such an elastic component may be a coil spring, and can play both the role of a releasable connection and of torque limiter against excessive tightening action which could result in a coring of the tissues.

More specifically, according to the aforementioned first aspect, the invention discloses a set of intracardiac capsules with its in situ implantation accessory, of the type disclosed by EP 2394695 A1 aforementioned, that is to say including an autonomous capsule with a cylindrical tubular body provided at its distal end by an anchoring member adapted to penetrate a tissue wall of a cavity of the heart, and an implantation accessory of this capsule. The implantation accessory includes a catheter with an inner lumen, extended at its distal end by a tubular protection tip defining an interior volume capable of housing the capsule, and disconnectable mechanisms for supporting and guiding the capsule to the implantation site.

Typically of the invention, the catheter is a remotely steerable catheter. The implantation accessory further includes a sub-catheter housed within the lumen of the remotely steerable catheter, and having a degree of freedom in translation and a degree of freedom in rotation relative to the remotely steerable catheter. The sub-catheter and the capsule are telescopically extendable with respect to the remotely steerable catheter between i) a retracted position wherein the capsule and its anchoring member are completely housed inside the tubular protection tip, and ii) a position wherein the capsule is deployed out of the tubular protection tip and is carried by the distal end of sub-catheter. Finally, the distal end of the sub-catheter and the proximal region of the capsule are provided with a first fastening mechanism for mutually securing in translation and in rotation. The fastening mechanism may be disconnectable under the effect of a rotation applied to the sub-catheter from the proximal end thereof In a preferred embodiment, the implantation accessory further includes a retaining wire housed in a lumen of the sub-catheter that links the capsule to the proximal end of the sub-catheter. The retaining wire is movable within the lumen of the catheter so as to allow removal of the latter, thereby leaving the capsule and the retaining wire in place. The proximal region of the capsule and the distal end of the retaining wire are provided with a second disconnectable fastening mechanism for securing in translation and in mutual rotation.

The retention wire may be a particular wire adapted to transmit rotational torque from its proximal end to its distal end, and the second fastening mechanism includes a rotational connection separable under the effect of said torque applied to the retaining wire, including a threaded element formed at the distal end of the retaining wire and cooperating with a threaded part formed at the proximal end of the capsule, or vice versa.

In a preferred embodiment, the first disconnectable fastening mechanism includes a deformable elastic component, such as a helical spring which cooperates with a rigid object, such as a central core on the capsule. The spring extends around the core such that it exerts on the latter a radial constriction effect, the spring and the core being configured to be disengaged under the effect of a torque applied to the spring at one end thereof, having the effect to reduce said radial constriction to release the core.

Preferably, the proximal end of the spring is secured to the distal end of the sub-catheter. The distal end of the spring is preferably free. The core is preferably an axial lashing rod carried by the proximal end of the capsule and secured in rotation with the latter.

When the capsule includes an anchoring screw, the direction of the coil spring is the same as that of the anchoring screw. The value of the torque applied to the spring that is effective to reduce said radial constriction to release of the core is determined. This torque value depends on the geometry of the spring and of the elasticity of the material which constitutes it, so as to be always lower that a predetermined limit value that is corresponding to a limit holding torque of the anchoring screw in the tissue of the implantation site, without coring of this tissue.

Furthermore, to allow the introduction of the assembly, it is possible to use a guidewire. In such embodiments, the protection tip then includes in the thickness of its peripheral wall a lateral lumen extending axially and opening at both the distal and proximal sides of the tip. This lumen being adapted to receive the guidewire and to allow the sliding thereon of the implantation accessory with the capsule housed in the protection tip. Finally, the protection tip preferably has at least one vent hole, and at least one radiopaque marker.

According to the aforementioned second aspect, the invention discloses an assembly of the type disclosed in EP 2394695 A1 cited above, particularly, including a medical device provided at its distal end with an anchoring member capable penetrating a tissue wall of a body, and an in situ implantation accessory of the medical device. The implantation accessory according to the present invention includes a deformable elongate tubular member having a disconnectable mechanism for support of the medical device and guiding of the medical device to a site of implantation. The disconnectable mechanism includes a helical spring cooperate with a central core and is suitable for securing in translational and in mutual rotation the tubular element of the implantation accessory and the medical device, and able to decouple the medical device with the tubular member of the implantation accessory under the effect of a rotation applied to the tubular member from the proximal end thereof.

Typically, the spring extends around the core with an adjustment such that it exerts on the latter a radial constriction effect, the spring and the core being capable of disengagement under the effect of a combined torque and traction applied to the spring at one end thereof, being effective to reduce said radial constriction to release the core.

Preferably, the proximal end of the spring is secured to the distal end of the tubular member of the implantation accessory, the distal end of the spring is free, and the core is an axial lashing rod carried by a proximal end of the medical device and secured in rotation to the latter.

When the medical device bears an anchoring screw, the direction of the coil spring is the same as that of the anchoring screw. The value of said torque applied to the spring that is effective to reduce said radial constriction to release of the core is determined. The torque value depends on the geometry of the spring and the elasticity of the material which constitutes it, so as to be always lower to a predetermined limit value, corresponding to a holding torque limit of the anchoring screw in the tissue of the implantation site, without coring of this tissue. Finally, the distal end of the spring is advantageously a rounded end.

According to another aspect of the invention, an intracardiac assembly includes an autonomous capsule including a cylindrical tubular body provided at its distal end with an anchoring member adapted to penetrate tissue of a wall of a cavity of a heart and an implantation accessory. The implantation accessory includes a subcatheter configured to be received by, and move in rotation and in translation relative to, a catheter. The subcatheter includes a first fastening mechanism to couple the distal end of the subcatheter to a proximal end of the autonomous capsule. The first fastening mechanism comprises a torque limitation system configured to limit the torque transmission capacity from the subcatheter to the autonomous capsules.

According to yet another aspect of the invention, a method for implanting a medical device includes introducing a medical device provided at its distal end with an anchoring member adapted to penetrate tissue of a wall of a cavity of a heart to a target location in a cavity of the heart, wherein a proximal end of the medical device is coupled to a distal end of a subcatheter with a first fastening mechanism, wherein the subcatheter and the medical device are introduced to the target location through a catheter. The first fastening mechanism comprises a torque limitation system to control the torque provided to the anchoring member. The method further includes rotating the subcatheter to engage the anchoring member with the tissue of the cavity of the heart to implant the anchoring member into the tissue. After implantation, rotation of the subcatheter continues in the same direction so as to generate an excess torque at the torque limitation system to thereby release the first fastening means and decouple the subcatheter from the medical device.

DETAILED DESCRIPTION

Figure 1:
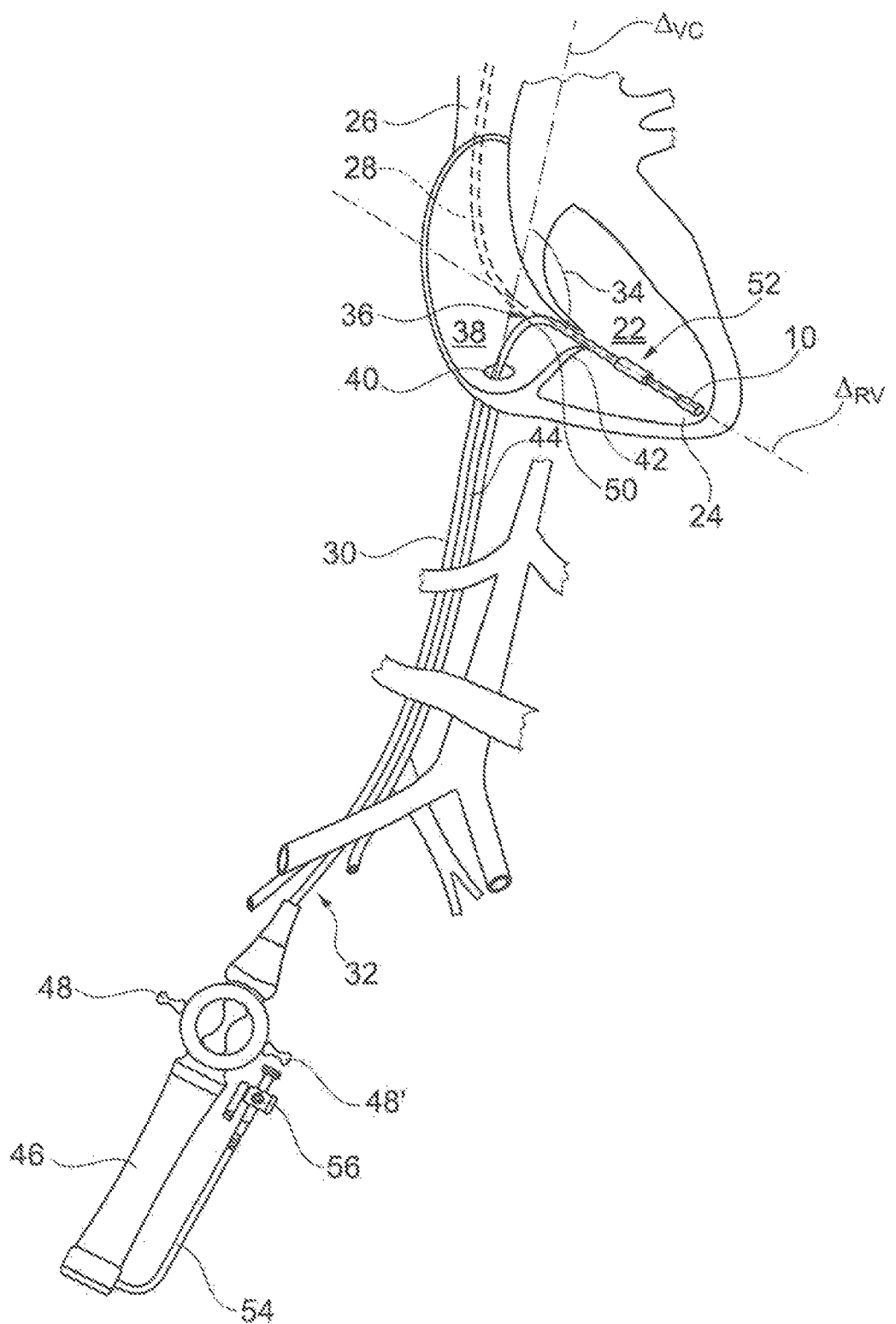
FIG. 1 illustrates the implantation accessory of the invention and its capsule, in position, with a schematic representation of the femoral approach and of the chambers of the heart.

An exemplary embodiment of the device of the invention will now be described. FIG. 1 illustrates a schematic representation of the femoral access route and the chambers of the heart, and depicting the implantation accessory according to the present invention bearing an autonomous capsule of the leadless type 10.

Such a leadless capsule (shown in more detail in particular in FIG. 11) includes a tubular body 12 provided at one of its ends with a projecting helical anchoring screw 14 axially extending from the tubular body and integral with it in rotation. The anchoring screw 14 includes in its distal portion a length of the order of 1.5 to 2 mm of non-contiguous turns, adapted to penetrate the heart tissue so as to secure the capsule there. The screw 14 can be an electrically active screw, comprising the detection/stimulation electrode at least at its distal end, or it can be a passive screw serving only to the anchoring of tubular body 12 in the wall of the heart chamber. In the latter case, the capsule is provided with an axial conductive needle 16 acting as a detection/stimulation electrode in contact with the myocardial tissue. Alternatively, it is also possible to provide a surface electrode.

The tubular body 12 includes various power supply circuits and methods for signal processing and wireless communication for the exchange of signals with a remote master device, implanted or not. These aspects are in themselves known, and since they are not part of the invention, they will not be described.

At its proximal end 18, the tubular body 12 of the capsule 10 includes an axial lashing rod 20 with a rounded end, the function of which will be described later in the implantation procedure. This lashing rod 20 is smooth on its outer face and has an internal threaded axial hole, a structure which will be explained in more detail with the description of FIG. 4 below.

The leadless capsule 10 is intended to be implanted in the right ventricle 22, especially at the bottom of the ventricle, in the region of the apex 24. For a conventional stimulation lead (connected to a remote generator), the location would typically be performed via the subclavian vein 26, as illustrated in dashed lines at 28, so that the end of the lead would be approximately oriented in the ΔRV axis of the right ventricle and thus could easily pass through the tricuspid valve and reach the apex of the ventricle 24. However, as mentioned in the introduction, this implantation approach is not feasible for implantation of leadless capsules, the dimensions and, in particular, the external diameter, being far superior to those of the head of a conventional lead.

It is therefore necessary to access, via the vena cava 30, from a femoral puncture 32. But in this case, the axis of approach, that is to say the ΔVC axis of the vena cava, has a strong angulation (angle 34) with the axis ΔRV of the right ventricle. Therefore, it is necessary to form a curvature 36 at the right atrium 38 in order to pass the implantation accessory emerging from the sinus 40 of the vena cava to the tricuspid valve 42 to then reach the cavity 22 of the right ventricle. Similar difficulties arise for implantation into the left ventricle, the implantation access then involving an arterial femoral puncture and the passage of the aortic arch.

Such a maneuver can be performed through a "steerable" catheter, with a catheter tube 44 handled from the proximal end by an operating handle 46 available to the practitioner. Using the handles 48, 48' the latter can create and adjust a curvature 50 to guide the distal end 52 of catheter 44 accurately, typically with an orientation up to 180° in both directions with a variable radius of curvature, of the order of 5 to 60 cm. The handle 46 is also provided with a purge drain lateral track 54 and of a valve 56, features which are in themselves entirely conventional.

With a conventional steerable catheter, if it is possible to precisely adjust the curvature 50, it is not possible to change the area of the catheter wherein, along its length, the curvature is formed. However, in the particular case illustrated with a femoral approach, with the objective of reaching the bottom of the right ventricle, this limitation can be troublesome with some specific morphologies with very elongated cavity. Indeed, the distal portion 52 of the steerable catheter located beyond the curvature of the region 50 may be too short to reach the region of the apex 24. Embodiments of the present invention address this difficulty, as will be explained hereinafter, so that the implementation of the invention is possible using a marketed, pre-existing, steerable conventional catheter to reduce the cost of the implantation accessory of the invention.

Figure 2:
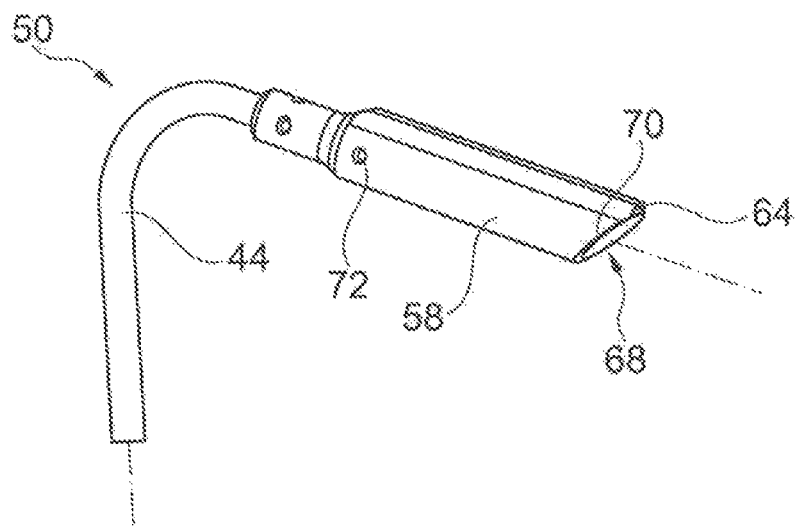
FIG. 2 shows the distal end of a remotely steerable catheter provided with its protection tip, in the retracted position of the leadless capsule.
Figure 3:
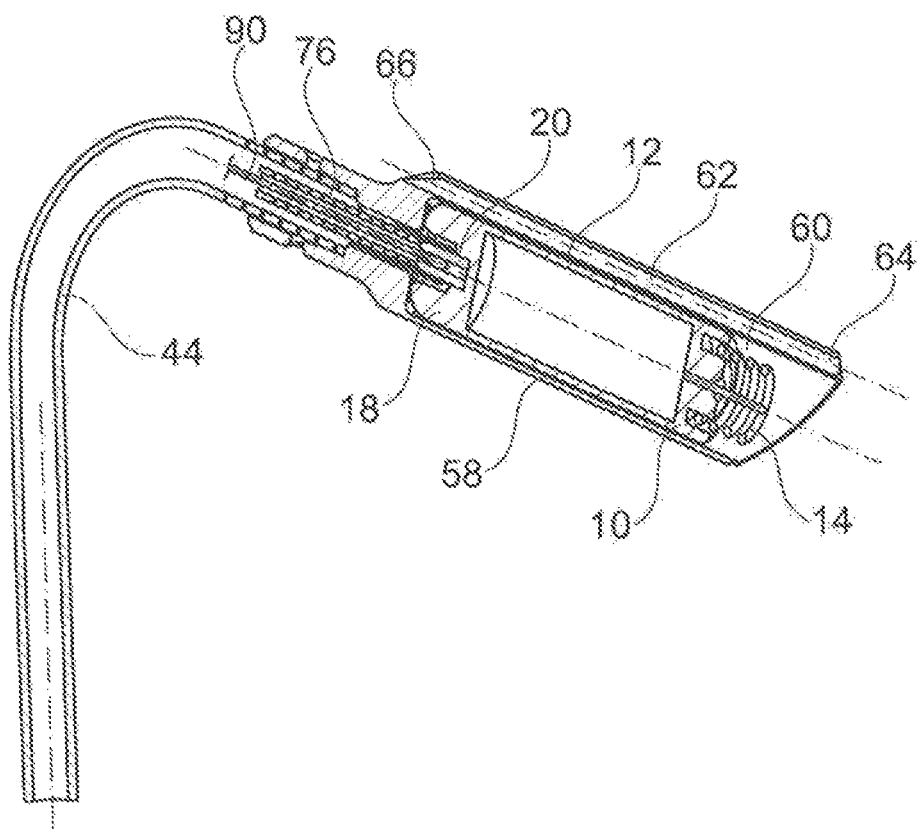
FIG. 3 is an enlarged, sectional view of FIG. 2, showing the general configuration of the various internal elements and the leadless capsule housed inside the protection tip.
Figure 4:
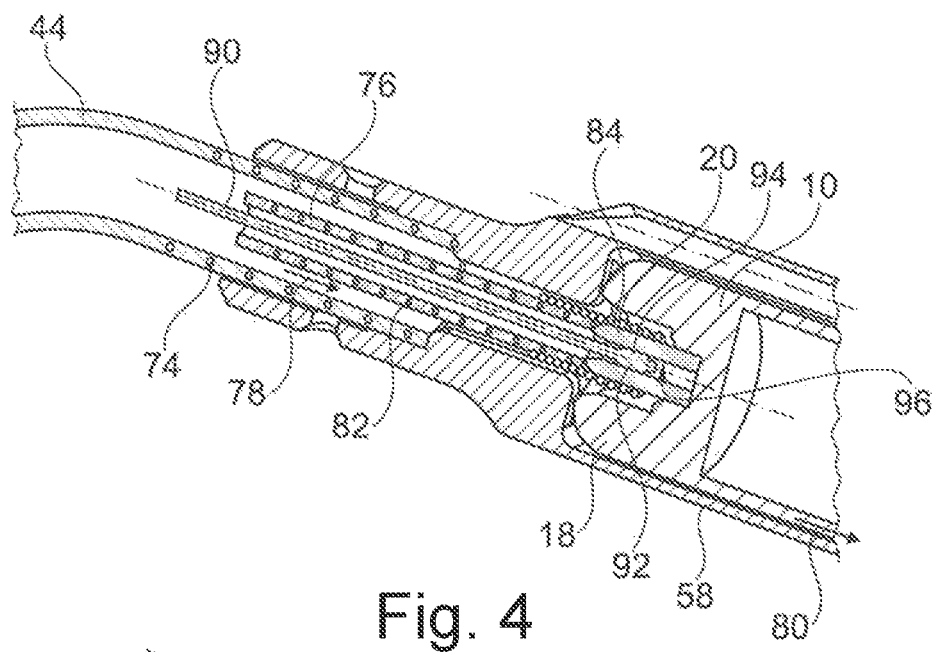
FIG. 4 is an enlarged view of the sectional view of FIG. 3, in the region of the connection with the proximal end of the leadless capsule.

FIGS. 2 to 4 show, in enlarged views, the distal end of the steerable catheter 44, with the different characteristic elements of the invention. The steerable catheter 44 is provided at its distal end with a tubular protection tip 58 having a central recess 60 (FIG. 3) for housing the capsule 10 in a configuration called "retracted position", corresponding to FIGS. 2-4. The main function of the tip 58 is to protect the capsule, including the anchoring screw 14, during the intravenous passage of curves, angulations, valves, etc. Conversely, the cap protects the tissue from the risk of stripping potentially caused by the movement of translation of the screw.

The outer diameter of the steerable catheter 44 is typically between 10 and 15 French (6.6 to 10 mm), for an inner lumen diameter of between 8 and 12 French (2.66 mm to 4 mm). The tubular tip 58 must be able to house the capsule and therefore have an inside diameter of about 21 French (7 mm). Furthermore, a catheter of this size must necessarily move into the venous system while being guided by a coiled guidewire previously introduced into the vasculature.

Figure 8:
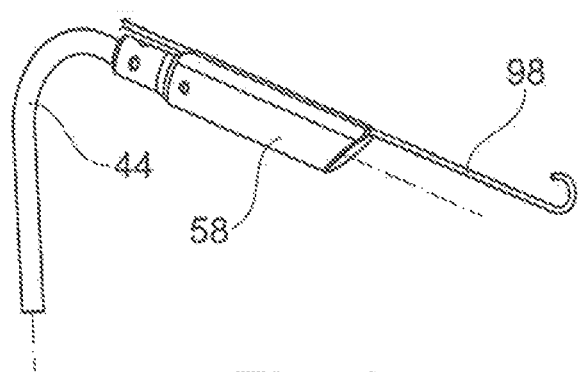
FIG. 8 shows the distal end of the remotely steerable catheter provided with its protection tip mounted on a coiled guidewire used to advance this tip from the femoral puncture until the selected implantation site.
Figure 9:
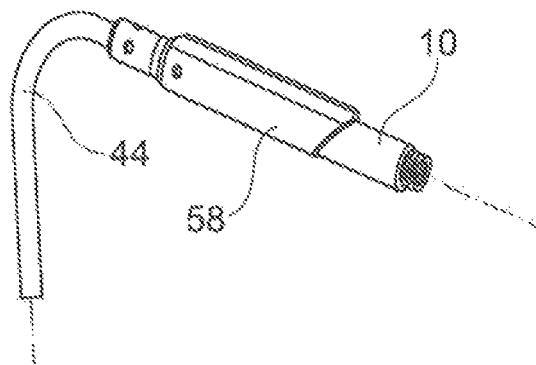
FIG. 9 shows the distal end of the remotely steerable catheter provided with its protection tip, with the leadless capsule partially emerged of this tip.

As in the illustrated design, the central canal of the catheter 44 is blocked by the capsule. To allow the introduction of a guidewire, the tubular tip is provided with an eccentric lateral lumen 62 extending axially the length of the tip and opening at the distal 64 and proximal 66 sides, preferably extending over the entire length of the tip 58. The inner diameter of the lateral lumen 62 allows for the introduction of a conventional coiled guidewire of a diameter of 3 French (1 mm), and the sliding of the tip, and therefore of the entire steerable catheter 44, through the vasculature (this configuration is notably shown in FIG. 8, wherein the reference 98 designates the coiled guidewire). Alternatively, the eccentric lateral lumen 62 may be extended along the body of the steerable catheter 44 to facilitate the pushing of the coiled guidewire and prevent any curling phenomenon thereof.

Note that the eccentricity of the lumen 62 combined to the beveled profile of the tip allows easy progression into the venous system by a "sidewire" technique. In addition, the front panel 68, the most distal area of the tip 58, is shaped to have a minimum front bearing surface to avoid any risk of perforation in case of accidental operation without the coiled guide.

In addition, a radiopaque marker 70 is provided in front of the tubular tip 58 on the most distal surface of this tip, to more efficiently identify the capsule outlet if the tip is made of a radio-transparent material. Finally, one or more drain holes 72 are disposed proximal to the tip, to prevent piston effect upon injection of contrast medium, which otherwise would result in pushing the capsule 10 out of the protection tip 58.

The catheter 44 is formed with a reinforced structure, such as a wire mesh or a coil embedded in the thickness of the catheter wall, so as to provide a torque transmission capability exerted on the proximal handle to the distal end (reinforced structure 74).

The implantation accessory of the invention further includes, typically, a sub-catheter 76, introduced into the central lumen of the steerable catheter 44, and movable in rotation and in translation relative to the latter. The function of this sub-catheter 76 is to ensure the deployment of the capsule out of the protection tip and to advance the capsule to the implant site by a translation movement over a sufficient length, typically from to 2 to 6 cm depending on the anatomy of the patient. In the figure, arrow 78 indicates the translation of the sub-catheter 76 within the steerable catheter 44, and arrow 80 indicates the translation of the capsule 10 out of the protection tip 58. The sub-catheter 76 also has the function of ensuring the transmission of torque from the proximal end (at the operating handle) to its distal end, and is provided for this purpose of a reinforced structure 82.

It is possible to use as the sub-catheter 76 a conventional guide catheter sized from 4 to 6 French (1.33 to 2 mm), which is an existing, simple and cost-saving device meeting the current constraints torque transmission, low coefficient of friction inside and outside, flexibility, etc. Sub-catheter 76 may have a proximal "Luer-Lok" connection for the rapid mounting of a multifunction adapter such as a rotational hemostasis valve or other adapter compatible with this sealed connection standard. Alternatively, the sub-catheter 76 can be used to inject a contrast to the back of the capsule 10 so as to accurately monitor the operation under fluoroscopy.

A fastening mechanism according to the present invention is directed to the coupling of an implantation device including a hollow or not elongated tubular member (such as a catheter) with an autonomous (such as a leadless capsule) or not (such a probe head of a pacing lead) medical device, said device being provided at its distal end with an anchoring mechanism adapted to penetrate a cardiac or else body tissue. The fastening mechanism according to the invention employs an elastic deformable component, such as helical spring 84, which is not used for its properties of elasticity in axial traction/compression (effect resulting from the elongation or the reconciliation of the coils of the spring), but for its radial compression properties, that is to say for the pinch or throttle effect can such a spring can exert around a rigid component, such as a core inserted into the helical form. In other embodiments, the elastic deformable component may be a lamella that provides radial compression about the core.

The geometry of the elastic deformable component, such as a spring, and the elasticity of the material which constitutes it are chosen so as to produce between the elastic component and the core, in the absence of external stress, an interference fit (caused by the radial compression resulting from the pinch effect). In the illustrated example of FIG. 4 of the leadless capsule 10, the core is constituted by the lashing rod 20 with rounded end, located axially on the proximal portion 18 of the capsule 10 and outwardly oriented. This lashing rod 20 may be shaped to optimize the disengagement function.

Figure 5:
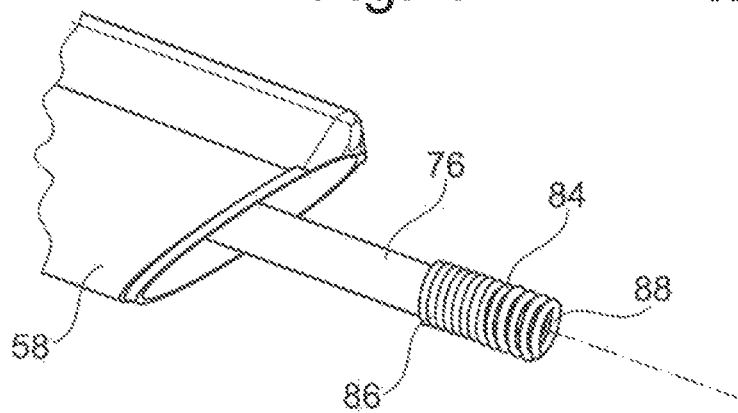
FIG. 5 separately shows the radial compression coil spring mounted on the end of the sub-catheter.
Figure 6:
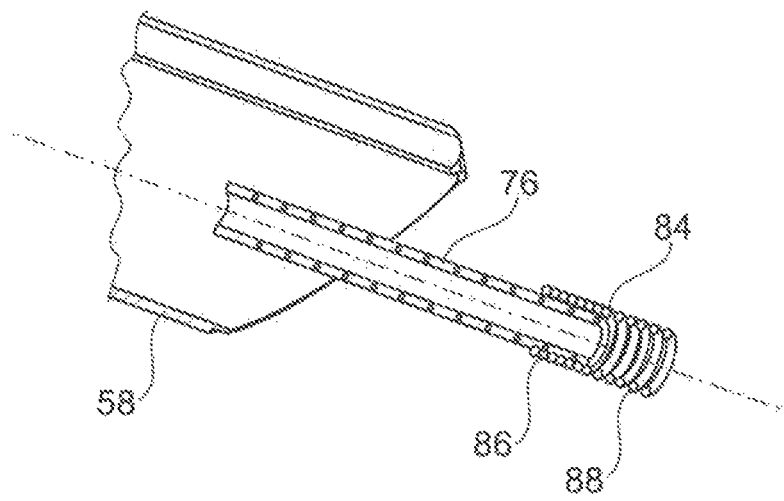
FIG. 6 is a sectional view corresponding to FIG. 5.
Figure 7A:
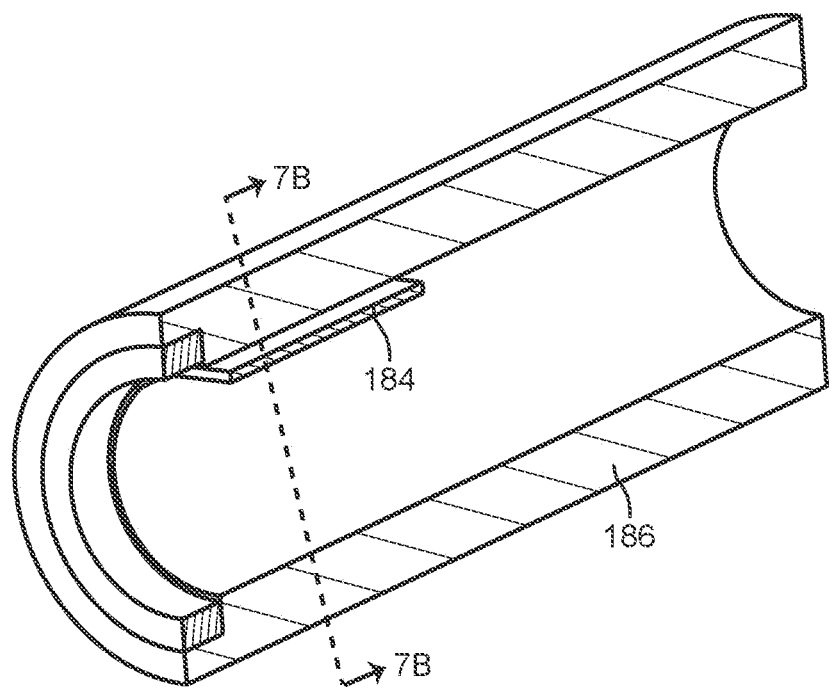
FIG. 7A is a sectional view showing a socket of a hollow cylinder housing a lamella.
Figure 7B:
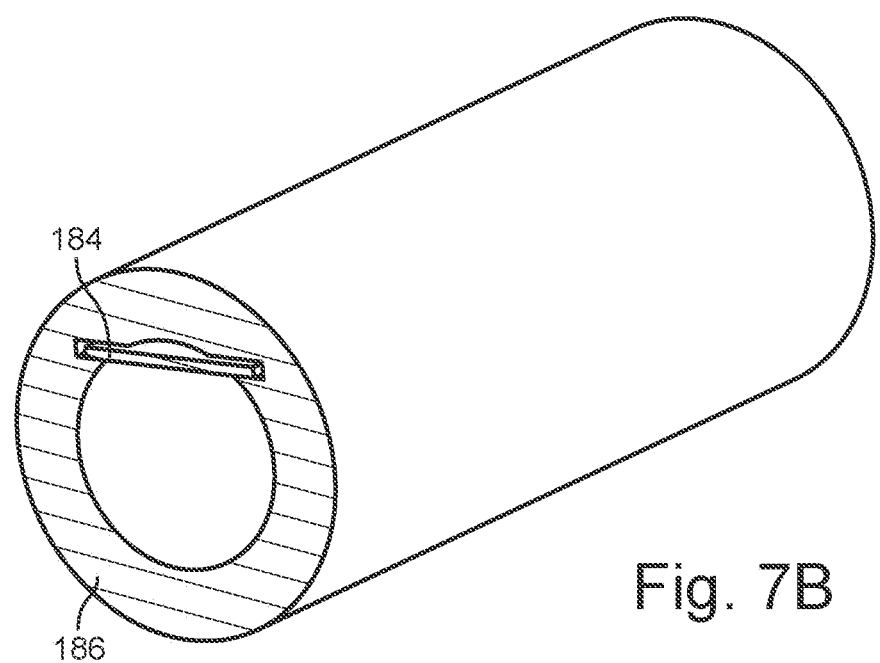
FIG. 7B is a sectional view corresponding to FIG. 7A.
Figure 7C:
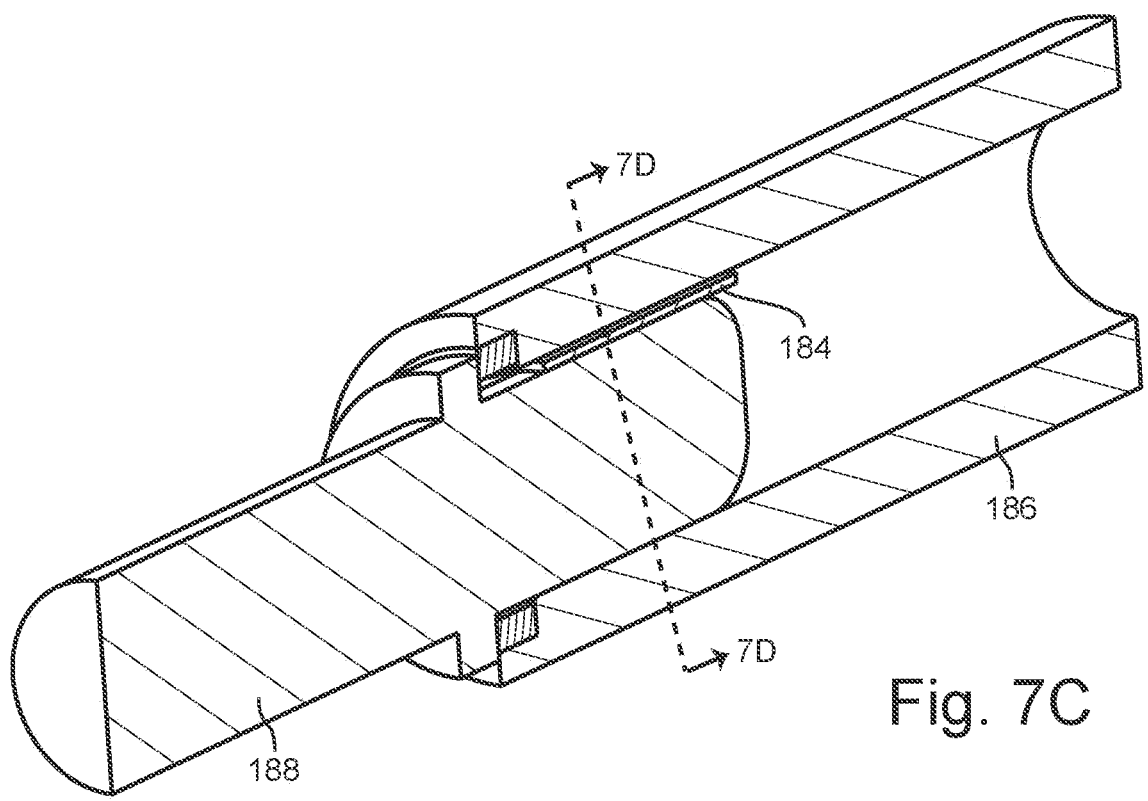
FIG. 7C is a sectional view of a non-deformable axis inserted into the hollow cylinder housing of FIG. 7A.
Figure 7D:
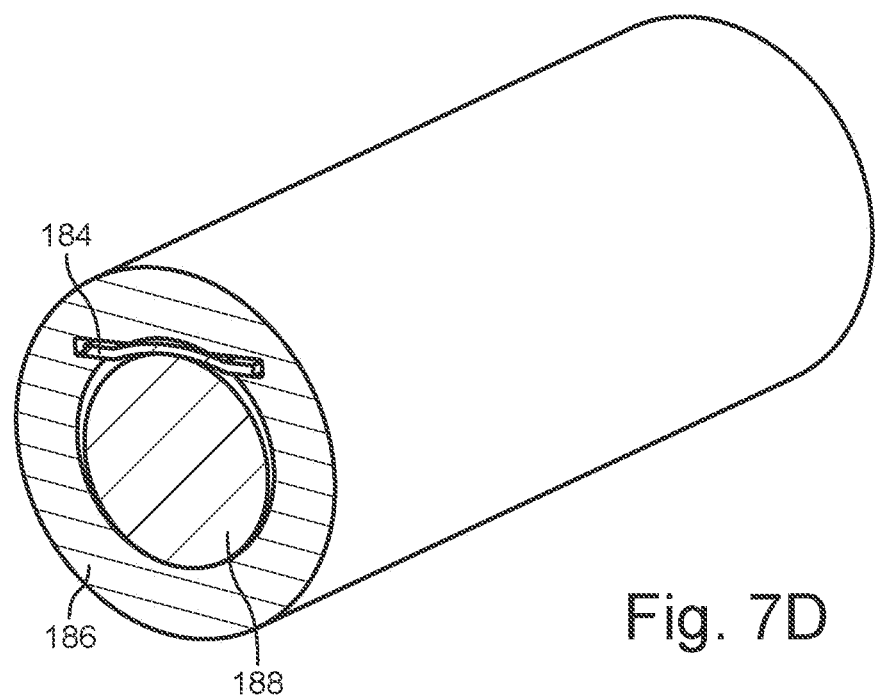
FIG. 7D is a sectional view corresponding to FIG. 7C.

The spring 84 is shown in detail and in isolation in FIGS. 5 and 6. The spring 84 is secured to the distal end of the sub-catheter 76 by turns 86. This securing in translation and in rotation, for example by welding or gluing, must be kept regardless of the degree of stress normally applied to the sub-catheter 76 and to the spring 84.

The turns 88 located distally of the spring 84 are free turns, which are surrounding the lashing rod 20 but which are not mechanically fastened to the latter by connection mechanisms other than interference fit with tightening obtained in the static configuration of these two elements. In addition, the distal end of the spring 84 is preferably a rounded end to prevent tissue injury and hang at various manipulations. The inactive turns 86 and/or the active turns 88 may be either touching or not contiguous.

Once the capsule 10 is fixed to the implant after complete penetration of the anchoring screw 14 to the front face of the capsule, the practitioner continues to make the sub-catheter 76 turn, thereby generating an excess torque. The excess torque has the effect of reducing the force exerted by the free turns 88 on the lashing rod 20, to cause rotational sliding of these turns on this same rod. By combining this rotational movement to a slight tensile load, the compression spring 84 is released from the lashing rod 20, by longitudinal sliding of the turns on the rod, thus releasing the capsule 10 from the spring 84, and thus from the sub-catheter 76.

In an alternative embodiment of the first fastening mechanism, shown in FIGS. 7A-7D, the deformable plastic member is a lamella 184 that is positioned in a socket created by a hollow cylinder 186. The lamella 184 is radially deformable relative to the cylinder axis. The rigid component is provided in the form of a non-deformable axis 188 configured to be introduced into the socket of the hollow cylinder 186. The introduction causes deformation of the lamella 184, thereby producing a radial force between the non-deformable axis 188 and the lamella 184, as shown in 7D. Relative rotational movement between the hollow cylinder 186 and the non-deformable axis 188 generates a tangential calibrated friction and therefore creates a limitation in the torque applied to the components of the system.

The radial compression spring 84 or lamella 184 thus act as torque limiter. Indeed, with the anchoring screw of a standard leadless capsule, if the practitioner continued rotation of the sub-catheter 76 and therefore of the capsule 10, the torque would increase and exceed a limit $C_{coring}$. This increases the risk of the anchoring screw locally tearing the tissues under the effect of the rotation of the screw advance thereof, causing a tearing of the tissues and, in the extreme, a perforation of the wall, with the risk of tamponade. This is not the case with the device and methods provided by the invention. The practitioner may indeed safely continue rotating the sub-catheter 76, always in the same direction (usually clockwise), because the extra torque due to the reaction of the anchoring screw anchored in the tissue is absorbed by the connection between, for example, the spring 84 and the lashing rod 20 (phenomenon of sudden increase of the torque when the front face of the capsule contacts the cardiac tissue). More specifically, the geometry and elasticity of the spring 84 are chosen so as to define a predefined torque $C_{release}$ lower to the coring limit, $C_{coring}$, corresponding to a limit holding torque of the anchoring screw in this tissue, without coring of the tissue, while providing a full screw (tissue contacting the front face of the capsule). Thus, when the $C_{release}$ torque is reached, the further rotation of the sub-catheter 76 in the clockwise direction causes, in combination with a slight traction force, the gradual release of the spring 84 with the lashing rod 20 by longitudinal sliding of the turns of the radial spring along the rod. In case of any excess torque, the turns of the radial spring slide in rotation on the securement ring therefore no longer transmit torque elevation. The clutch release torque $C_{release}$ is adjusted to a typical value of about 0.01 to 0.05 N·cm.

Furthermore, in a static configuration, the pinch force of the free portion 88 of the spring 84 on the lashing rod 20 is selected so as to prevent accidental disassembly by a traction force (axially directed force) lower to a sufficient threshold, typically a threshold which provides holding even for a traction exerted on the sub-catheter 76 under a force of up to 20 N.

Note also that if it is desirable to unscrew the capsule, for example because after a first implantation it is found that the electrical performance of the site are not satisfactory, the coupling system by the spring 84 will have no release effect during unscrewing. Since the spring will then be driven in reverse rotation (usually counterclockwise), this will further increase the effect of the tightening of the turns 88 of the lashing rod 20.

Another advantage of the spring 84 is after the release of the capsule, the implantation device is present with a screw at its end in the form illustrated in FIGS. 5 and 6. In particular, the free turns 88 of the spring 84 form a screw. In case of reoperation intraoperative, that is to say, if it is desirable to secure the new sub-catheter 76 to the capsule, the screw formed by the spring 84 will have the advantage of requiring no angular adjustment to secure the lashing rod 20 of the capsule to be retrieved (unlike the systems using a male/female connector which require positioning to allow the interlocking of the two elements).

Finally, note that the torque limiter comprising spring 84 is conveniently located in the chain of transmission of forces. Specifically, any loss of fidelity in the transmission of torque between the proximal end of the sub-catheter 76 (that is to say from the handle manipulated by the practitioner) and its distal end (the location of the coupling spring 84) has no effect on the maximum or minimum torque at the interface between the anchoring screw and the tissue, which is a guarantee of complete fixation. This is not the case for a detachable system that would be located further upstream, typically in the operating handle 46. Note also that all of these features are obtained via a very economical component of very simple and compact design.

The release of the capsule may thus be effected by a combined screwing and traction movement in two steps. First, screwing of the capsule in the heart wall, by clockwise rotation of the sub-catheter 76 (e.g. 10 rpm) under a slight push. Second, release of the capsule by a further clockwise rotation of the sub-catheter 76 (e.g. 5 turns) under slight tension to allow removal of the sub-catheter after release of the spring 84. To obtain this result, the direction of the turns of the spring is of course selected in the same direction as that of the anchoring screw, preferably with a right-engaging thread, so that the screwing of the capsule and then its release correspond to a rotation of the sub-catheter 76 in the clockwise direction, the most conventional one.

Advantageously, the implantation kit also includes a security thread or retainer 90 of "breadcrumb" wire-type connected to the capsule 10 on the distal side, extending over the entire length of the sub-catheter 76 and exceeding it proximally, that is to say on the side of the operating handle 46.

Figure 11:
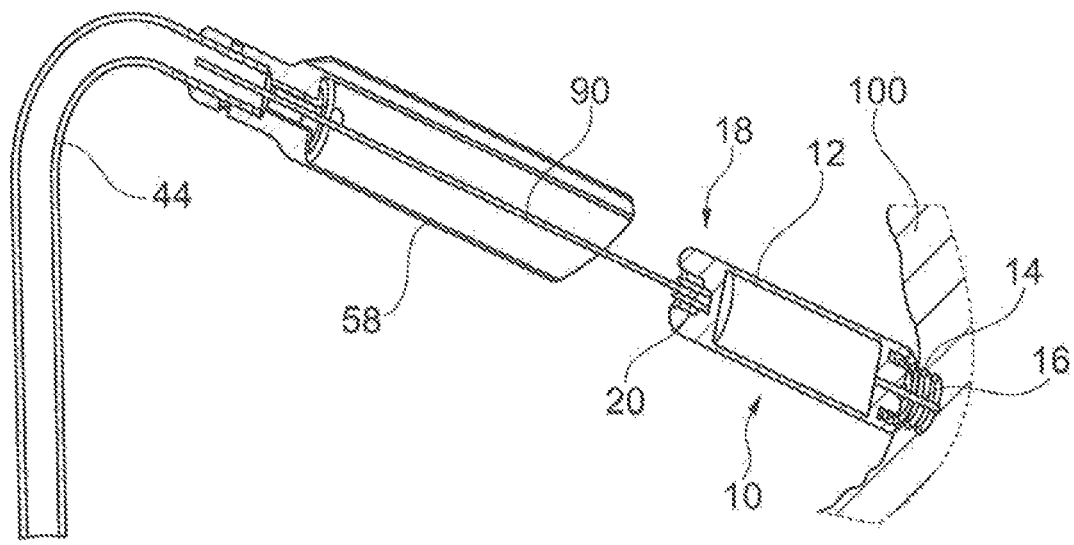
FIG. 11 is an enlarged and sectional homologous view of FIG. 10, once the capsule is implanted in the chosen site, after removal of the sub-catheter and with the retaining wire still in place.
Figure 12:
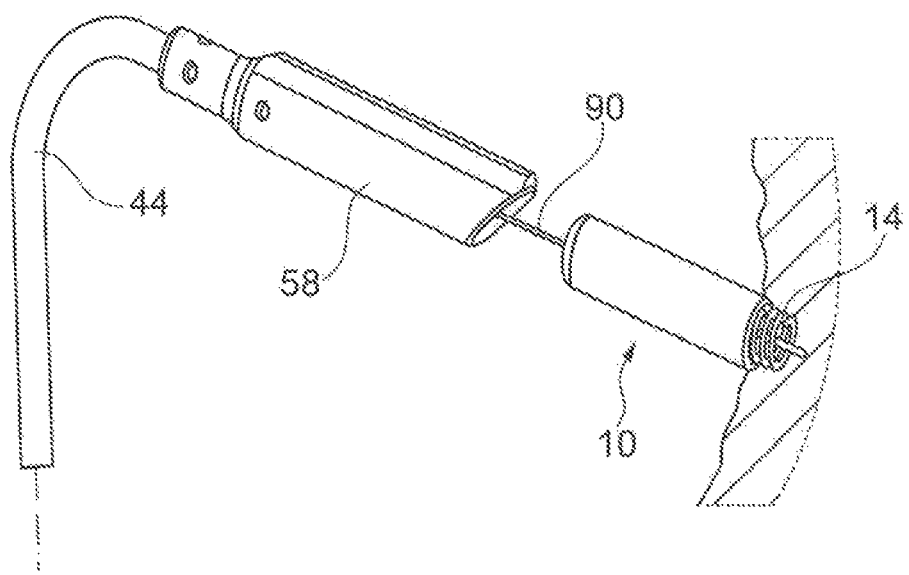
FIG. 12 shows the final configuration of the capsule and the implantation accessory in the situation corresponding to that of FIG. 11.

As shown in FIGS. 11 and 12, once the capsule 10 is implanted and dropped, its operation is tested, including the establishment of good wireless communication between the capsule and the remote master device as well as the stimulation electrical performance.

Once the steerable catheter 44 and the sub-catheter 76 are completely removed, the retaining wire allows for intraoperatively retrieving the capsule, with reintroduction of the implantation accessory by making it slide along the retaining wire until the protection tip 58 caps the capsule. The latter can then be re-coupled to the sub-catheter by a clockwise rotation (the clutch-limiter functionality being always effective). The capsule can then be unscrewed from the wall 100 by a counterclockwise rotation and repositioned at another site by the same principle as what has been described above, by a clockwise rotation of the sub-catheter.

The retaining wire is for example a wire of 1 French diameter (0.43 mm) having at its distal end 92 a thread 94 able to cooperate with a mating internal thread 96 formed in a threaded axial bore of the stowage axis 20 (FIG. 4). This retaining wire is preferably sufficiently flexible in its distal part (6 to 8 cm), while being able to transmit to the distal end 92 an unscrewing torque resulting from a rotation exerted from the proximal end, at the operating handle. Note that, because of the very small diameter of the screwing system 94, 96, the torque to be exerted to produce the unscrewing is very small (of the order of 0.02 N·cm), and may not in any way exert trigger a rotation movement of the capsule 10 which is firmly secured to the heart wall by the anchoring screw. The retention wire may be colored in different colors for each of the implanted capsules, so as to more easily identify the appropriate capsule in the event of reoperation.

The technique of the invention therefore provides triple security through the release system which allows at the release of the capsule:

To ensure complete screwing of the capsule in the tissue;
To prevent coring of the heart wall; and
To ensure the practitioner to recover the capsule after dropping in case of difficulty, through the retaining wire.

Figure 10:
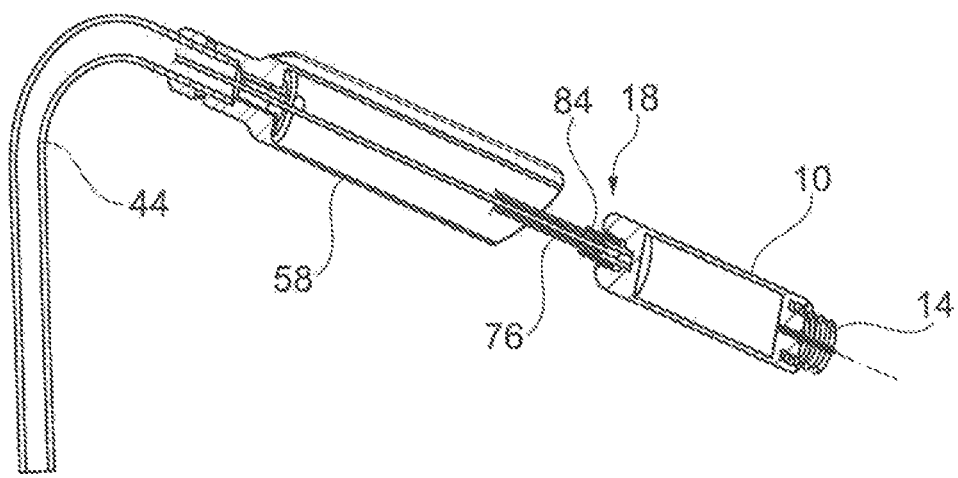
FIG. 10 is an enlarged, sectional view of FIG. 9, showing the general configuration of the different internal elements.

The procedure for setting up the leadless capsule through the implantation accessory as described above comprises the following steps, each of which is relatively conventional and can be easily performed by a practitioner without requiring special skills or additional maneuvers:

Right or left femoral puncture, in order to access the inferior vena cava 30;
Optional percutaneous introduction of a 23 French haemostatic introducer (7.66 mm);
Insertion of the steerable catheter 44 on a spiral guidewire (illustrated at 98 in FIG. 8), typically a 3 French (1 mm) guidewire on which the tubular tip 58, and thus the steerable catheter 44 will slide and move to the right atrium 38;
Turning maneuver of the tip of the steerable catheter 44 (as shown at 36 in FIG. 1) and introduction of the tip 58 in the right ventricle;

Release of the capsule 10 to the apex of the ventricle by translation of the sub-catheter 76 in the steerable catheter 44 (configuration shown in FIG. 10);

Visualization of the cardiac walls by injection of contrast medium through the sub-catheter;

Fine positioning of the capsule to the selected target site, with the possibility of translation once in the cardiac cavity by a more or less important deployment of the sub-catheter 76 from the steerable catheter 44, allowing fine adjustment to suit a wide variety of anatomies;

Screwing of the capsule in the heart wall to the release of the radial compression spring 84;

Separation of the sub-catheter 76 with the capsule 10, and removing of the sub-catheter 76 out of the steerable catheter 44 (configuration shown in FIG. 11);

Electrical test of the capsule;

Complete removal of steerable catheter 44 and of the sub-catheter 76;

Final release of the capsule, with withdrawal of the retaining wire 90 by low torque unscrewing; and Closure of the puncture site.

What is claimed is:

1. An implantation accessory comprising:
a steerable catheter with an inner lumen, comprising at its distal end a tubular protection tip defining an interior volume configured to house a capsule;
a disconnectable attachment mechanism for supporting and guiding the capsule to an implantation site; and
a subcatheter housed within the lumen of the steerable catheter with a degree of freedom in translation and a degree of freedom in rotation relative to the steerable catheter;
wherein the subcatheter is telescopically extendable relative to the steerable catheter; and
wherein the subcatheter is provided with a first fastening mechanism for fastening the sub-catheter and the capsule in translation and in mutual rotation, and
wherein the first fastening mechanism comprises a helical spring cooperating with a central core of the capsule, the spring extending around the core such that the spring exerts a radial constriction on the central core, the spring and the core being disengageable under an effect of a combined torque and traction applied to the spring at one end of the spring, the combined torque and traction effective to reduce the radial constriction until release of the core.

2. The implantation accessory of claim 1, further comprising:
a retaining wire housed in the lumen of the subcatheter, the retaining wire being movable within the lumen of the catheter so as to permit removal thereof while leaving in place the capsule and the retaining wire, a distal end of the retaining wire being provided with a second fastening mechanism for securing the capsule and the retaining wire in translation and mutual rotation, the second fastening mechanism being disconnectable.

3. The implantation accessory of claim 2, wherein the retaining wire is a wire adapted to transmit a rotational torque from its proximal end to its distal end, and the second fastening mechanism comprises a screw mechanism separable under the effect of said torque applied to the retaining wire, this screw mechanism comprising a threaded member formed at the distal end of the retaining wire.

4. The implantation accessory of claim 1, wherein a proximal end of the spring is secured to the distal end of the subcatheter, a distal end of the spring is free, and the core is an axial lashing rod.

5. The implantation accessory of claim 1, further comprising a guidewire, wherein the protection tip comprises in its peripheral wall a lateral lumen extending axially and having an opening at each of distal and proximal edges of the tip, the lumen being capable of receiving the guidewire, and wherein the protection tip comprises in its distal region a beveled front face.

6. The implantation accessory of claim 1, wherein the protection tip comprises at least one vent hole.

7. The implantation accessory of claim 1, wherein the protection tip comprises at least one radiopaque marker.

8. The implantation accessory of claim 1, wherein the spring is an elastic deformable component and the core is a rigid component, wherein the spring and the core are configured to slide relative to one another in a slide movement.

9. The implantation accessory of claim 8, wherein the slide movement between the spring and the core is a longitudinal slide movement.

10. The implantation accessory of claim 1, wherein a force of the radial compression creates an interference fit between the spring and the core.

11. The implantation accessory of claim 1, wherein the first fastening mechanism is located in a distal part of the subcatheter.

12. An implantation accessory, comprising:
a subcatheter configured to be received by, and move in rotation and in translation relative to, a catheter, wherein the subcatheter comprises a first fastening mechanism configured to couple a distal end of the subcatheter to an autonomous capsule;
wherein the first fastening mechanism comprises a torque limitation system configured to limit a torque transmission capacity from the subcatheter to the autonomous capsule, the torque limitation system comprising a helical spring cooperating with a central core of the autonomous capsule, the spring extending around the core such that the spring exerts a radial constriction on the central core, and the spring and the core being disengageable under an effect of a combined torque and traction effective to reduce the radial constriction until release of the core.

13. The implantation accessory of claim 12, wherein the first fastening mechanism is configured to disconnect the subcatheter from the autonomous capsule when continued rotation is applied to the subcatheter after implantation.

14. The implantation accessory of claim 12, wherein the spring is an elastic deformable component and the core is a rigid component, wherein the spring and the core are configured to slide relatively to one another in a slide movement.

15. The implantation accessory of claim 14, wherein the slide movement between the spring and the core is a longitudinal slide movement.

16. The implantation accessory of claim 14, wherein the slide movement between the spring and the core is a rotational slide movement.

17. The implantation accessory of claim 12, wherein a force of the radial compression creates an interference fit between the spring and the core.

18. The implantation accessory of claim 12, wherein the torque limitation system is located in a distal part of the subcatheter.

19. A method for implanting a medical device, comprising:
- introducing a medical device to a target location in the cavity of the heart, wherein a proximal end of the medical device is coupled to a distal end of a subcatheter via a first fastening mechanism, wherein the subcatheter and the medical device are introduced to the target location through a catheter;
- wherein the first fastening mechanism comprises a torque limitation system to control a torque provided to medical device, the torque limitation system comprising a helical spring cooperating with a central core of the medical device, the spring extending around the core such that the spring exerts a radial constriction on the central core, and the spring and the core being disengageable under an effect of a combined torque and traction applied to the spring at one end of the spring, the combined torque and the traction effective to reduce the radial constriction until release of the core;
- rotation the subcatheter to engage the medical device with the tissue of the cavity of the heart to implant the medical device into the tissue; and
- after implantation, continuing rotation of the subcatheter in the same direction so as to generate an excess torque at the torque limitation system to thereby release the first fastening mechanism and decouple the subcatheter from the medical device.

20. The method of claim 19, wherein the torque limitation system is configured to control the torque without torque losses occurring between a proximal end of the subcatheter and the distal end of the subcatheter.

* * * * *